(12) United States Patent
Brogan et al.

(10) Patent No.: US 8,295,925 B2
(45) Date of Patent: Oct. 23, 2012

(54) METHODS AND DEVICES FOR TREATING NEUROPATHY AND LOSS OF PROTECTIVE SENSATION

(75) Inventors: Michael S. Brogan, Buffalo, NY (US); Laura E. Edsberg, Newfane, NY (US); Douglas P. Kalinowski, Newstead, NY (US); Laura L. Deming, Lunenburg, MA (US)

(73) Assignee: WaveRx, Inc., Waltham, MA (US)

( * ) Notice: Subject to any disclaimer, the term of this patent is extended or adjusted under 35 U.S.C. 154(b) by 539 days.

(21) Appl. No.: 12/474,527

(22) Filed: May 29, 2009

(65) Prior Publication Data

US 2010/0145413 A1 Jun. 10, 2010

Related U.S. Application Data

(60) Provisional application No. 61/057,162, filed on May 29, 2008.

(51) Int. Cl.
*A61N 1/00* (2006.01)

(52) U.S. Cl. .......................................... 607/2; 607/144

(58) Field of Classification Search ................. 607/2, 61, 607/68, 72, 144, 153
See application file for complete search history.

(56) References Cited

U.S. PATENT DOCUMENTS

| | | | |
|---|---|---|---|
| 4,417,590 A | 11/1983 | Smith et al. | |
| 4,846,181 A | 7/1989 | Miller | |
| 4,982,742 A | 1/1991 | Claude | |
| 6,607,550 B1 | 8/2003 | Bertwell | |
| 7,150,710 B2 | 12/2006 | Haber et al. | |
| 2005/0234525 A1 | 10/2005 | Phillips | |
| 2006/0106427 A1 | 5/2006 | Brogan et al. | |
| 2010/0324611 A1* | 12/2010 | Deming et al. | 607/2 |

OTHER PUBLICATIONS

International Search Report from corresponding PCT Application No. PCT/US2009/45598 mailed Jul. 27, 2009.

* cited by examiner

*Primary Examiner* — Brian T Gedeon
(74) *Attorney, Agent, or Firm* — Lando & Anastasi, LLP

(57) ABSTRACT

Certain embodiments described herein are directed to methods for treating loss of protective sensation. In certain embodiments, loss of protective sensation may be restored by application of an effective amount of a pulsed current at, for example, an effective pulse frequency. Devices and systems designed to treat loss of protective sensation are also described.

23 Claims, 6 Drawing Sheets

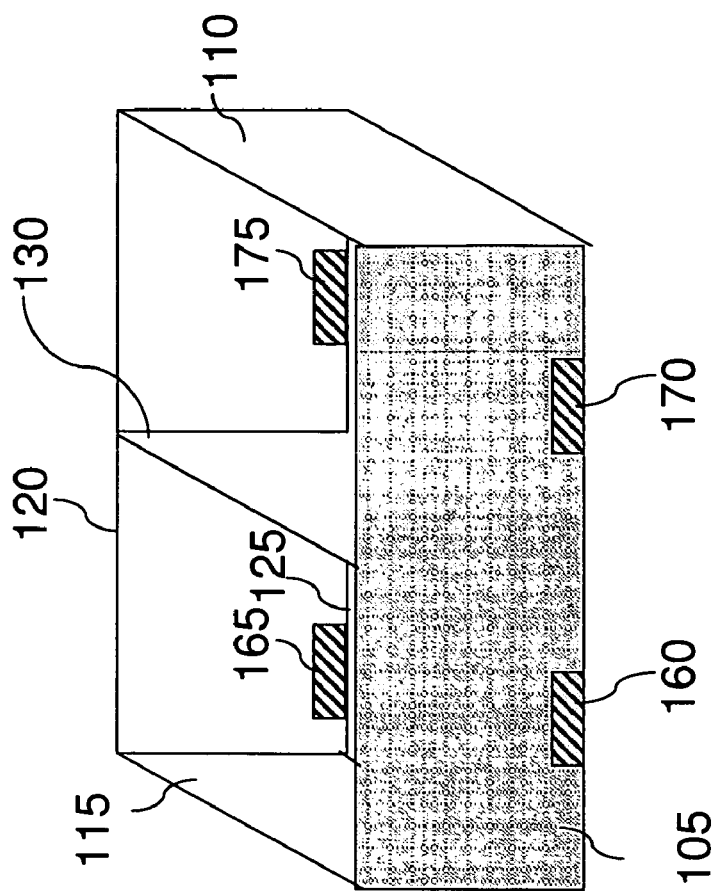
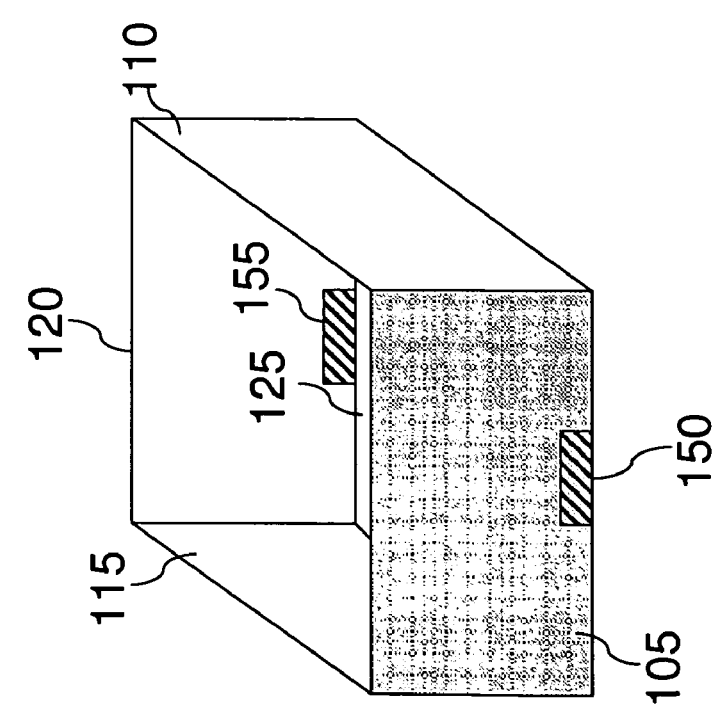
FIG. 1B
FIG. 1A

METHODS AND DEVICES FOR TREATING NEUROPATHY AND LOSS OF PROTECTIVE SENSATION

PRIORITY APPLICATION

This application claims priority to U.S. application Ser. No. 61/057,162 filed on May 29, 2008, the entire disclosure of which is hereby incorporated herein by reference for all purposes.

TECHNOLOGICAL FIELD

Certain embodiments described herein are directed to methods and devices that are designed to treat neuropathy or to treat or prevent loss of protective sensation (LOPS) in areas of the body (e.g., loss of protective sensation associated with neuropathy from, for example, diabetes) including, for example, the hands and feet.

BACKGROUND

Loss of protective sensation is a condition commonly experienced by the elderly, those with poor circulation and many people with diabetes. Diabetic subjects, in particular, are at risk for losing sensation in their extremities. Protective sensation is important because it allows people to sense changes in the top and/or bottom of the foot and in other appendages. If loss of protective sensation goes unnoticed, blisters and sores can form on the feet (or other areas) which can ultimately lead to infection and possible amputation. Better devices and methods are needed to treat loss of protective sensation.

SUMMARY

In a first aspect, a method of treating loss of protective sensation, for example, loss of protective sensation associated with neuropathy, is provided. In certain examples, the method comprises identifying an area with loss of protective sensation (or neuropathy) on a foot of a subject. In some examples, the method comprises placing the area in a footbath comprising a first electrode and a second electrode, to immerse the area in a fluid in the footbath, and to couple the foot to the first electrode and the second electrode. In other examples, the method comprises providing an effective amount of a current to the area using the first electrode and the second electrode to treat the loss of protective sensation in the area of the foot. In some examples, the loss of protective sensation can be associated with neuropathy, e.g., diabetic neuropathy.

In another aspect, a method of treating loss of protective sensation of an area of an appendage of a subject is disclosed. In certain examples, the method comprises coupling the area of the appendage to a first electrode and a second electrode, and providing an effective amount of a current to the coupled area through the first and second electrodes to selectively target sensory nerve fibers in the area of the appendage to treat the loss of protective sensation. In some examples, the loss of protective sensation can be associated with neuropathy, e.g., diabetic neuropathy.

In an additional aspect, a method of treating neuropathy, e.g., loss of protective sensation or loss of protective sensation associated with neuropathy, in an area of an appendage of a subject comprising providing an effective amount of a pulsed current to the area with the loss of protective sensation, the pulsed current provided at an effective pulse pair frequency to selectively target sensory nerve fibers. In some examples, the pulse pair frequency can be selected to target the sensory nerve fibers without substantial targeting of pain nerve fibers to treat the loss of protective sensation in the area is described.

In another aspect, a footbath for treating loss of protective sensation of an area on a foot of a subject is provided. In certain examples, the footbath comprises a reservoir comprising a front wall, sidewalls coupled to the front wall, a back wall coupled to the sidewalls and a bottom surface coupled to the front wall, the sidewalls and the back wall to provide a substantially fluid tight reservoir. In some examples, the footbath may also include a first electrode in the reservoir and a second electrode in the reservoir. In certain embodiments, the footbath can include a circuit electrically coupled to the first electrode and the second electrode and configured to provide a pulsed current at an effective pulse pair frequency to the first electrode and the second electrode to couple the first and second electrodes to the area of the foot and to selectively target sensory fibers in the area of the foot to treat the loss of protective sensation. In certain examples, the loss of protective sensation that is treated using the footbath can be loss of protective sensation associated with neuropathy, e.g., diabetic neuropathy.

In an additional aspect, a sock for treating loss of protective sensation on an area of a foot of a subject is described. In certain examples, the sock comprises a toe segment, a heel segment, a plantar segment extending between the toe segment and the heel segment, a dorsal segment extending between the heel segment and the toe segment and connected to the plantar segment, a first electrode in the sock and a second electrode in the sock. In some examples, the sock can also include a circuit electrically coupled to the first electrode and the second electrode and configured to provide a pulsed current at an effective pulse pair frequency to the first electrode and the second electrode to couple the first and second electrodes to the area of the foot and to selectively target sensory fibers in the area of the foot to treat the loss of protective sensation. In some examples, the loss of protective sensation that is treated using the sock can be loss of protective sensation associated with neuropathy, e.g., diabetic neuropathy.

In another aspect, a glove for treating loss of protective sensation on an area of a hand of a subject is provided. In certain examples, the glove comprises at least one finger receptacle, a palm surface and a back surface each extending from the finger receptacle to a wrist portion, a first electrode in the glove, and a second electrode in the glove. In certain embodiments, the glove can also include a circuit in the glove and configured to provide a pulsed current at a pulse pair frequency to the first electrode and the second electrode to couple the first and second electrodes to the area of the hand and to selectively target sensory fibers in the area of the hand to treat the loss of protective sensation. In certain examples, the loss of protective sensation that is treated using the glove can be loss of protective sensation associated with neuropathy, e.g., diabetic neuropathy.

In an additional aspect, a method of facilitating treatment of loss of protective sensation is provided. In certain examples, the method comprises providing a footbath sized and arranged to receive one or both feet of the subject, the footbath comprising a reservoir comprising a front wall, sidewalls coupled to the front wall, a back wall coupled to the sidewalls and a bottom surface coupled to the front wall, the sidewalls and the back wall to provide a substantially fluid tight reservoir, providing a first electrode and a second electrode, and providing instructions to use the footbath to provide a pulsed current through the first and second electrodes to an area of the foot to treat the loss of protective sensation. In certain examples, the loss of protective sensation that is treated using the footbath can be loss of protective sensation associated with neuropathy, e.g., diabetic neuropathy.

In another aspect, a method of facilitating treatment of loss of protective sensation, comprising providing a sock comprising a toe segment, a heel segment, a plantar segment extending between the toe segment and the heel segment, a dorsal segment extending between the heel segment and the toe segment and connected to the plantar segment, providing a first electrode and a second electrode, and providing instructions to use the sock to provide a pulsed current through the first and second electrodes to the area of a foot to treat the loss of protective sensation is disclosed. In certain examples, the loss of protective sensation that is treated using the sock can be loss of protective sensation associated with neuropathy, e.g., diabetic neuropathy.

In an additional aspect, a method of facilitating treatment of loss of protective sensation comprising providing a glove comprising at least one finger receptacle, a palm surface and a back surface each extending from the finger receptacle to a wrist portion, providing a first electrode and a second electrode, and providing instructions to use the glove to provide a pulsed current through the first and second electrodes to the area of the hand to treat the loss of protective sensation is disclosed. In certain examples, the loss of protective sensation that is treated using the glove can be loss of protective sensation associated with neuropathy, e.g., diabetic neuropathy.

In another aspect, a method of facilitating treatment of loss of protective sensation comprising providing a sleeve configured to encompass an appendage comprising an area with loss of protective sensation, providing a first electrode and a second electrode, and providing instructions to use sleeve to provide a pulsed current through the first and second electrodes to the area to treat the loss of protective sensation is described. In certain examples, the loss of protective sensation that is treated using the sleeve can be loss of protective sensation associated with neuropathy, e.g., diabetic neuropathy.

In an additional aspect, a method of facilitating treatment of loss of protective sensation comprising providing a bandage configured to be placed on an area with loss of protective sensation, providing a first electrode and a second electrode, and providing instructions to use the bandage to provide a pulsed current through the first and second electrodes to the area to treat the loss of protective sensation is disclosed. In certain examples, the loss of protective sensation that is treated using the bandage can be loss of protective sensation associated with neuropathy, e.g., diabetic neuropathy.

In another aspect, a method of facilitating treatment of loss of protective sensation comprising providing a wrap configured to be positioned around an area to be treated for the loss of protective sensation and configured to contact itself to retain the wrap around the area to be treated for the loss of protective sensation, providing a first electrode and a second electrode, and providing instructions to use the bandage to provide a pulsed current through the first and second electrode to the area to treat the loss of protective sensation is described. In certain examples, the loss of protective sensation that is treated using the wrap can be loss of protective sensation associated with neuropathy, e.g., diabetic neuropathy.

In an additional aspect, a kit for treating loss of protective sensation in an area of a foot comprising a footbath sized and arranged to receive one or both feet of the subject, the footbath having a reservoir comprising a front wall, sidewalls coupled to the front wall, a back wall coupled to the sidewalls and a bottom surface coupled to the front wall, the sidewalls and the back wall to provide a substantially fluid tight reservoir, and instructions to use the footbath to provide a pulsed current through a first electrode and a second electrode in the footbath to the area of the foot to treat the loss of protective sensation is disclosed. In certain examples, the footbath of the kit can be configured or used to treat loss of protective sensation associated with neuropathy, e.g., diabetic neuropathy.

In another aspect, a kit for treating loss of protective sensation in an area of the foot comprising a sock comprising a toe segment, a heel segment, a plantar segment extending between the toe segment and the heel segment, a dorsal segment extending between the heel segment and the toe segment and connected to the plantar segment, and providing instructions to use the sock to provide a pulsed current through a first electrode and a second electrode in or on the sock to the area of a foot to treat the loss of protective sensation is described. In certain examples, the sock of the kit can be configured or used to treat loss of protective sensation associated with neuropathy, e.g., diabetic neuropathy.

In an additional aspect, a kit for treating loss of protective sensation on an area of a hand comprising a glove comprising at least one finger receptacle, a palm surface and a back surface each extending from the finger receptacle to a wrist portion, and instructions to use the glove to provide a pulsed current to a first electrode and a second electrode in or in contact with the glove to the area of the hand to treat the loss of protective sensation is disclosed. In certain examples, the glove of the kit can be configured or used to treat loss of protective sensation associated with neuropathy, e.g., diabetic neuropathy.

In another aspect, a kit for treating loss of protective sensation comprising a sleeve configured to encompass an appendage comprising an area with loss of protective sensation, and instructions to use the sleeve to provide a pulsed current through a first electrode and a second electrode in or on the sleeve to the area to treat the loss of protective sensation is described. In certain examples, the sleeve of the kit can be configured or used to treat loss of protective sensation associated with neuropathy, e.g., diabetic neuropathy.

In an additional aspect, a kit for treating loss of protective sensation comprising a bandage configured to be placed on an area with loss of protective sensation, and instructions to use the bandage to provide a pulsed current through a first electrode and a second electrode in or on the bandage to the area to treat the loss of protective sensation is disclosed. In certain examples, the bandage of the kit can be configured or used to treat loss of protective sensation associated with neuropathy, e.g., diabetic neuropathy.

In another aspect, a kit for facilitating treatment of loss of protective sensation comprising a wrap configured to be positioned around an area to be treated for the loss of protective sensation and configured to contact itself to retain the wrap around the area to be treated for the loss of protective sensation, and instructions to use the wrap to provide a pulsed current through a first electrode and a second electrode in or on the wrap to the area to treat the loss of protective sensation is described. In certain examples, the wrap of the kit can be configured or used to treat loss of protective sensation associated with neuropathy, e.g., diabetic neuropathy.

Additional aspects, features and examples are described in more detail below.

BRIEF DESCRIPTION OF THE FIGURES

Certain specific aspects, features and examples are described in more detail below with reference to the accompanying figures in which:

FIG. 1A is an illustration of a footbath including a single fluid compartment, in accordance with certain examples;

FIG. 1B is an illustration of a footbath including two fluid compartments, in accordance with certain examples;

Figure 2:
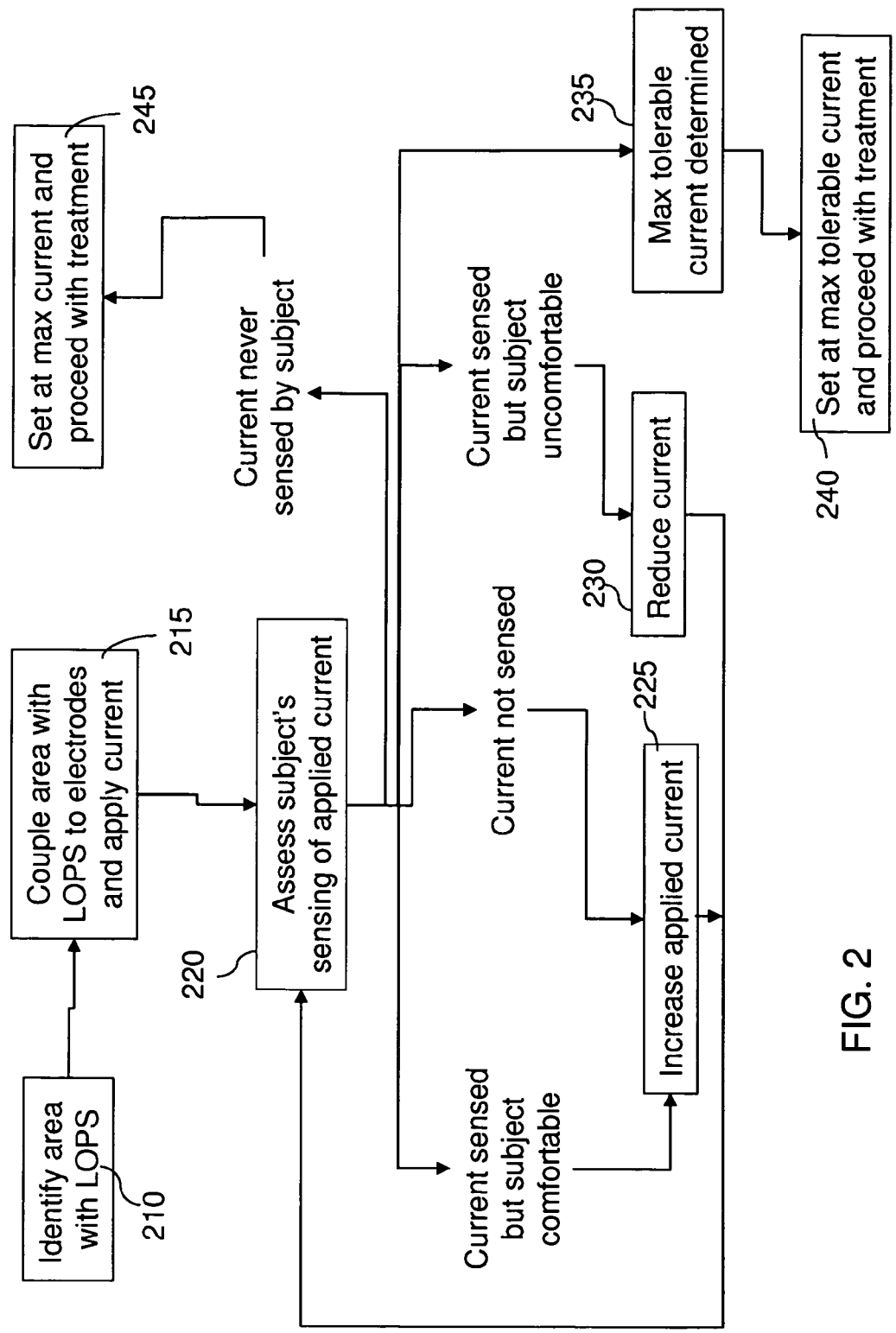
FIG. 2 is a flow chart of a protocol to determine the current to be used for treating loss of protective sensation, in accordance with certain examples.

It will be recognized by the person of ordinary skill in the art, given the benefit of this disclosure, that the dimensions of the devices shown in the figures are not to scale. Certain dimensions may have been enlarged or otherwise distorted to facilitate a better understanding of the technology described herein.

DETAILED DESCRIPTION

The technology described herein can be used to treat neuropathy or neuropathic conditions such as, for example, loss of protective sensation, e.g., loss of protective sensation associated with diabetic neuropathy, in many different areas of the body. For ease of illustration, certain embodiments are described below with reference to areas on the feet, hands, arms or other appendages. However, the methods and devices can be used with other areas to treat loss of protective sensation (or neuropathy) in those areas. In addition, the current applied herein to effectuate treatment may be applied in the absence of any drug or therapeutic to provide restoration, to at least some degree, of the loss of protective sensation using application of the current itself.

In many people with diabetes, there can be associated nerve loss or damage leading to peripheral neuropathy. See, for example, Zochodne, D. W. "Diabetes Mellitus and the Peripheral Nerve System: Manifestations and Mechanisms." Muscle Nerve 36: 144-166, 2007. Peripheral sensory neuropathy is a strong risk factor for both foot ulceration and amputation. See Armstrong et al. "Choosing a Practical Screening Instrument to Identify Patients at Risk for Diabetic Foot Ulceration," Arch, Internal Med. 1998: 158: 289-292. Other articles that discuss the risks and complications that can result from diabetic neuropathy include, but are not limited to, C. F. Corbett. "Practical Management of Patients With Painful Diabetic Neuropathy," The Diabetes Educator 2005; 31; 523; A. J. M. Boulton, "Whither Clinical Research in Diabetic Sensorimotor Peripheral Neuropathy," Diabetes Care, Vol. 30, No, 10, October 2007; and C. H. M. van Schie. "Neuropathy: mobility and quality of life," Diabetes/Metabolism Research and Reviews, 2008; 24 (Suppl 1): S45-S51. Khaodir et al., "Enhancing Sensation in Diabetic Neuropathic Foot with Mechanical Noise," Diabetes Care, Vol. 26, No. 12, December 2003 describes specific targeting to improve fine touch sensitivity using low levels of noise. The entire disclosure of each of these articles is hereby incorporated herein by reference in its entirety.

Certain embodiments disclosed herein are directed to devices, systems and methods for treating neuropathic conditions that are configured to provide a voltage or current to, or near, an area of a subject where the neuropathic condition may be present. Such voltage or current can be provided using a pair of electrodes or a plurality of electrodes depending on the exact configuration of the device. Neuropathy is a condition whereby deranged function and structure of peripheral motor, sensory, and/or autonomic neurons, involving either the entire neuron or selected levels, may occur. There are many different types of neuropathy including, but not limited to, polyneuropathy, mononeuropathy, mononeuritis multiplex and autonomic neuropathy. The most common form is (symmetrical) peripheral polyneuropathy, which mainly affects the feet and legs.

The devices, systems and methods disclosed herein may be used to treat any one or more of these types of neuropathy but are particularly designed to treat loss of protective sensation, e.g., loss of protective sensation associated with neuropathy, for example, diabetic neuropathy. Certain embodiments described herein are designed to treat protective sensation loss by restoring, to at least some degree, protective sensation that may be associated with one or more disease states, e.g., diabetes, nerve degeneration, poor circulation or the like. For example, many subjects with diabetes may have or develop poor or no sensation in the feet. These same subjects often have ulcerations and/or infections develop on a foot due to, for example, poor circulation, weakened immune systems or poor overall health. Without any appreciable protective sensation in their feet, the ulcerations may go unnoticed leading to infection and eventual amputation of the foot. The methods and devices described herein can treat such sensation loss (or other neuropathic conditions) to reduce the likelihood that any infection or ulcerations go unnoticed, which should decrease the chances of eventual amputation of the foot. The exact mechanism that restores the protective sensation remains unclear, but application of a current may reduce edema, increase localized blood circulation, enhance the growth of nerve tissue or restore the function of non-functioning nerves, which may lead to improvements in the protective sensation.

In certain embodiments, a method of treating loss of protective sensation comprising identifying an area having loss of protective sensation on an appendage of a subject, e.g., a foot, a hand, a leg, an arm, is described. The loss of protective sensation in a particular area may be evaluated using several different tests. Some of these tests use a monofilament to identify an area or areas of the appendage with reduced or no protective sensation. One such test that can be used is known as the 10-g Semmes-Weinstein Monofilament test. In this test, a monofilament exerts 10 grams of force when bowed into a C-shape against the skin for one second. Patients who cannot reliably detect application of the 10-g monofilament to designated sites of an appendage are considered to have lost protective sensation at that site. Patients with diabetes who have lost protective sensation of a foot, as measured by standardized testing with the 10-g monofilament, are at significantly increased risk to develop a foot ulcer that can lead to subsequent lower extremity amputation. The 10-g monofilament test can be repeated at different areas of the appendage to identify some or all of those areas where loss of protective sensation has occurred. Such identified areas may be treated using the methods and devices described herein.

In one embodiment, the area or areas to be treated may be placed in a suitable fluid reservoir that includes a first electrode and a second electrode. Depending on the particular appendage where the area is located, the fluid reservoir may take different forms. Where the area to be treated is located on a foot, the fluid reservoir may take the form of a footbath, as shown in FIG. 1A. Referring to FIG. 1A, the footbath includes a front wall 105, sidewalls 110, 115, a back wall 120, and a bottom surface 125. The front wall 105 is connected to the sidewalls 110, 115. The sidewalls 110, 115 are connected to the back wall 120, and the bottom surface 125 is connected to each of the front wall 105, the sidewalls 110, 115 and the back wall 120 to provide a substantially fluid tight reservoir, e.g., one that fluid does not leak out. The fluid reservoir may optionally include at least one inner wall 130 (FIG. 1B) to divide the fluid reservoir into two or more fluid compartments each sized and arranged to receive a single appendage, e.g., a single foot or a single hand. Referring again to FIG. 1A, the footbath may include a first electrode 150 and a second electrode 155, which can be coupled to the area to be treated. The electrodes can be integrated into the foot bath or can be added to the footbath. Where the divided footbath in FIG. 1B is used, each compartment may include its own pair of electrodes such as, for example, electrodes pairs 160, 165 and 170, 175, respectively. When the electrodes are coupled to the area to be treated, the area could be in contact with at least one of the electrodes, the area could be adjacent to the electrodes, the area could be on a foot or hand that is in contact with at least one of the electrodes, or the area could be on a foot or hand that is adjacent to the electrodes. In particular, the area can be coupled to the electrodes by many different placements and positions so that current from the electrodes can be provided to the area to be treated. For example, the fluid reservoir can receive a fluid that can be used to immerse the area or the entire appendage in the reservoir prior to and during treatment to couple the area to the first and second electrodes.

In certain embodiments, the footbath may include more than two electrodes. For example, while two electrodes are shown in FIG. 1A, more than two electrodes can be used to increase the current density provided to the area to be treated. In addition, the exact placement of the electrodes relative to the placement of the area to be treated can vary. In some examples, the electrodes may be placed at the sides of the foot, whereas in other examples, one electrode can be placed at the toes and the other electrode can be placed at the heel of the foot. In some examples, the electrodes can be mounted on a track or slide so that they are independently moveable to position the electrodes adjacent to or on the area to be treated.

In certain examples, once the area to be treated is placed in the fluid reservoir, an effective amount of current can be provided to treat the loss of protective sensation. In certain embodiments, the effective amount of current selectively targets sensory nerve fibers to treat the loss of protective sensation without substantial targeting or stimulus of nerve pain fibers. For example, the waveform, pulse frequency and other current parameters can be selected so that the sensory nerves associated with loss of protective sensation are selectively targeted to treat the loss of protective sensation. In certain examples, the maximum current used can be determined by calibrating the device prior to initializing treatment. For improved treatment, it can be desirable that the maximum tolerable current be used in the treatment provided that the current does not exceed a safe maximum current, e.g., about 50 or 100 milliamperes. An illustrative calibration flow chart is shown in FIG. 2. In a step 210, an area of a subject having loss of protective sensation is identified as described herein. The identified area is then coupled to electrodes and a current is applied in step 215. The subject's ability to sense the current is assessed at step 220. If the current is sensed but the subject is comfortable, then the current is increased at step 225 and the subject's ability to sense the increased current is reevaluated at step 220. The current is incrementally increased up to a maximum current or up to the point where the current is sensed but the subject is uncomfortable. Similarly, if the initially applied current is not sensed by the subject, the current is increased at step 225 and the subject's ability to sense the current is reevaluated at step 220. If the subject is uncomfortable, then the applied current is reduced at step 230 and the subject's ability to sense the reduced current is assessed at step 220. This process is repeated until the maximum tolerable current is identified at step 235 and then the treatment is initiated at step 240. In subjects who have entirely lost their protective sensation, the applied current may never be sensed. In such instances, the current can be set at a maximum current and treatment may be initiated at step 245.

Figure 3:
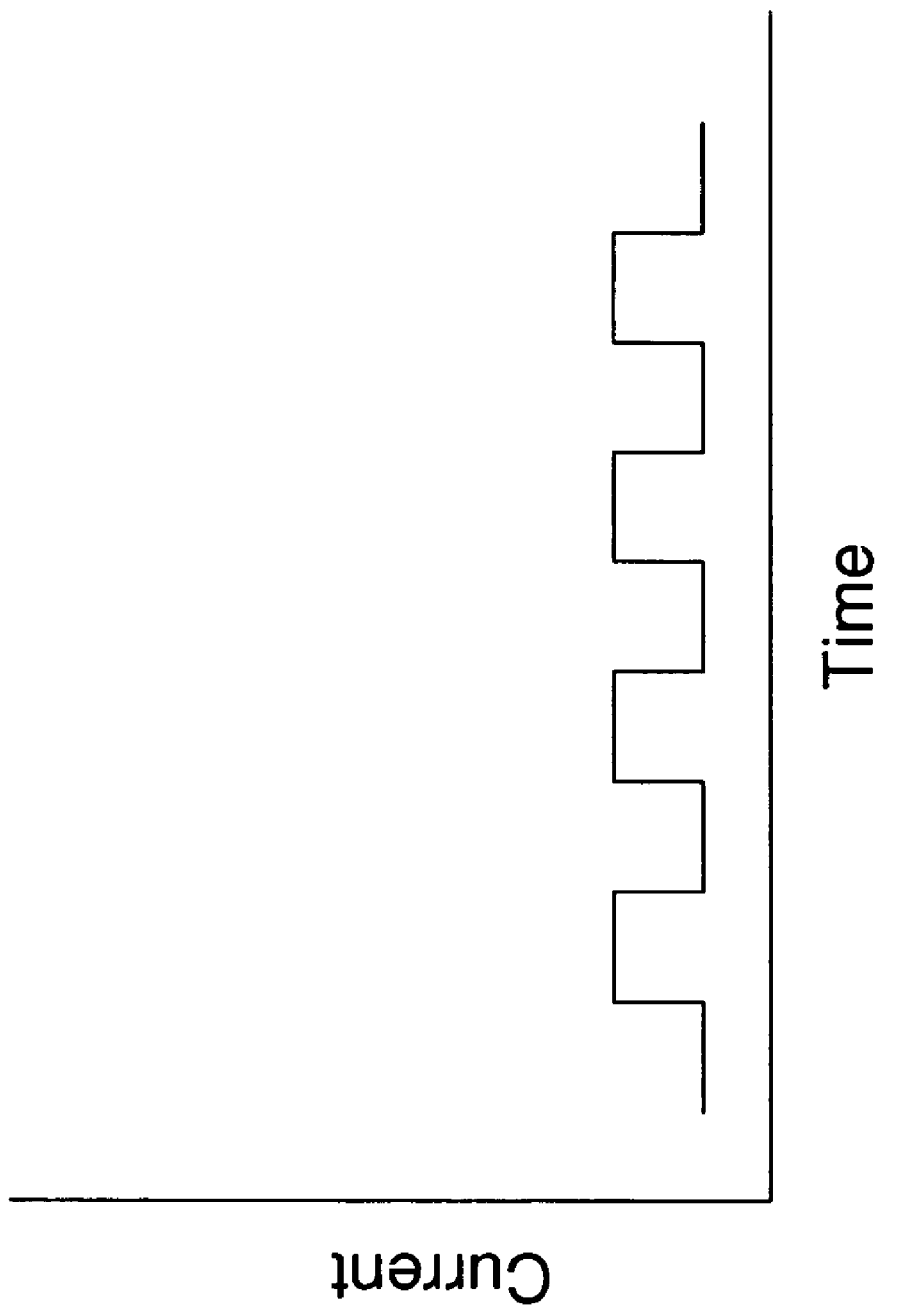
FIG. 3 is an illustration of a monophasic pulsed current, in accordance with certain examples.

In certain embodiments, once the appropriate current for treatment is determined, an effective amount of the current can be provided to the area through the first and second electrodes to treat the loss of protective sensation (or other neuropathic conditions). The type of current can vary and in certain examples the current may be a direct current, an alternating current, a continuous current or a pulsed current. For example, in certain embodiments the applied current may take the form of a direct current that is applied at less than 50 milliamperes, e.g., in either a continuous or pulsed form. In certain examples, the direct current can be applied using a voltage source less than 150 volts. In certain embodiments, the direct current can be applied at an intensity of less than 3 milliamperes, e.g., 500 microamperes to 3 milliamperes. In some examples, the direct current may be cycled between a fully on state, e.g., up to about 150 volts, and a fully off state, e.g., down to about 0 volts. The duration at which the current remains in the on state and the off state can vary and by cycling between the two states a current pulse can be generated. In certain embodiments, the effective amount of current is provided using a monophasic pulsed current. An example of a monophasic pulsed current is shown in FIG. 3. The monophasic pulsed current resembles a square wave where the current rises to a set "on" value for a selected duration and then falls to an "off" value for a selected duration prior to rising again. In some examples, the intensity of the current may vary from about 500 microamperes to about 100 milliamperes, more particularly about 1 millampere to about 100 milliamperes, for example about 20 milliamperes to about 100 milliamperes, 500 microamperes to about 50 milliamperes or about 20 milliamperes to about 50 milliamperes.

In certain embodiments, the delay between pulses may vary from about 100 microseconds to about 500 microseconds, more particularly about 150 microseconds to about 400 microseconds, for example, the delay or distance apart of the pulse pairs may be from about 150 microseconds to about 350 microseconds, e.g., 150-330 microseconds.

The exact on-time or width of the pulse may also vary. In some embodiments, the pulse width may vary from about 1 microsecond to about 100 microseconds, more particularly about 3 microseconds to about 75 microseconds, for example about 4-60 microseconds, 5-50 microseconds 10-50 microseconds or 20-40 microseconds. The pulses may be repeated at a selected frequency such as, for example, 50-100 Hz, 55-90 Hz or 60-80 Hz. Where pulse pairs are considered, the pulse pair frequency may be, for example about 80-300 Hz, more particularly about 90-250 Hz, for example about 100-200 Hz. In some examples, the pulse pair frequency may be at least about 100 Hz, e.g., about 100 Hz to about 300 Hz, to selectively target sensory nerve fibers, e.g., the pulse pair frequency can be selected to target sensory nerve fibers without substantial targeting of pain nerve fibers, which are typically targeted at much lower frequencies. In certain examples, the pulsed current can be provided using a monophasic waveform at an intensity between about 500 microamperes to about 50 milliamperes, depending on the intensity that the subject can tolerate, in pulse pairs about 150-330 microseconds apart, with a pulse width between about 5-50 microseconds and a pulse pair repeat frequency of about 100-200 Hz.

In certain embodiments, the current may be provided for a selected duration. For example, once the treatment current is determined, the total treatment time may vary from about 15 minutes to about 45 minutes per treatment. Each treatment session may be repeated at a desired schedule. For example, treatment may be performed once daily, twice daily, three times daily, once per week, twice per week, three times per week, four times per week, five times per week, six times per week or every day each week. The total duration of treatment may last one week or more, e.g., one week, two weeks, three, weeks, four weeks, one month, two months, three months, four months, five months, six months or anytime between these illustrative periods. In certain embodiments, a treatment regimen can consist of providing the current once per day for thirty minutes, five times per week for a period of six weeks.

In certain examples, the current intensity and other current parameters may be varied during treatment and may change from treatment to treatment. For example, a subject may be able to tolerate higher current levels than those initially tolerated at the beginning of treatment. Where the initial current is set at a low level based on subject tolerance, the current can be increased after a delay period, e.g., 5, 10 or 15 minutes, to ascertain whether or not the higher current level is now tolerable by the subject. Alternatively, during treatment the subject may become uncomfortable and it can be desirable to reduce the current intensity during treatment to a comfortable level. Such adjustments can be made by the operator during treatment. In some instances, the system can be programmed to periodically adjust the current to a higher or lower level for a selected period to provide a "burst" of a different current to improve treatment outcomes.

In certain embodiments, the electrodes of the footbaths shown in FIGS. 1A and 1B may be electrically coupled to a power source such as, for example, those commercially available from Rich-Mar, Naimco, and Bioinduction to provide the current to the electrodes and to the area to be treated. The exact type of power source is not critical and many different types of power sources can be used. In some examples, the power source can be integrated into the footbath or can be an "on-board" power source such as a disposable or rechargeable battery or batteries. In addition, the particular materials used for the electrodes, whether used in a footbath or with the other devices described herein, is not critical and many different materials such as, for example, stainless steel and conductive metals and non-metals can be used in the electrodes. The circuits described herein can be integrated into the footbath or can be part of the power source depending on the desired configuration of the device.

In certain embodiments, when the footbath is used, one or more fluids may be placed in the footbath prior to application of a current. The fluid need not cover the entire foot but instead can be added at a suitable volume to immerse the affected area in the fluid. In some instances, enough fluid can be added so that the entire feet and both malleoli are entirely submerged in the fluid. Treatment may then be initiated by providing an effective amount of current as described herein.

In certain examples, the fluid added to the footbath may be water, e.g., tap water, to facilitate use of the footbath in a home setting. A user can fill the footbath to a desired level or to a mark on the side of the footbath prior to initiating treatment. The electrodes of the footbath can then be electrically coupled to a power source, e.g., a current source, and treatment may be performed. Alternatively, a user may place or position the electrodes in the footbath at desired sites prior to electrically coupling the electrodes to the power source. In some instances it may be desirable to include one or more agents in the water to further assist in the treatment or to simultaneously treat other disorders of the area. For example, one or more depolarizing agents may be added to fluid in the footbath to decrease the resistance during delivery of the current. In operation, the electrodes of the devices cause the water to undergo electrolysis. Hydrogen ions are formed at the surface of the cathode, which can lead to increased resistance to current flow and reduce overall performance. By adding a suitable depolarizing agent, the hydrogen ions can combine with one or more groups of the depolarizing agent to ensure the cathode retains its intended performance characteristics. One desirable depolarizing agent is a peroxide such as, for example, hydrogen peroxide, which can readily undergo reduction to generate oxygen and combine with the hydrogen ions at the cathode to form water. Other desirable depolarizing agents include those that can generate oxygen for combining with the hydrogen ions at the electrode. Illustrative other depolarizing agents include, but are not limited to, air, oxygen, ozone, and other substances which can act to neutralize positive charged species.

In certain embodiments, one or more antimicrobials or antifungals can be added to the fluid prior to the treatment. The use of an antimicrobial may be particularly desired where there are one or more ulcerations on the feet that are at risk of infection. The antimicrobial may be charged such that application of the current can act to drive the charged antimicrobial into the skin or the antimicrobial may be uncharged. Where an antifungal is used to treat, for example, tinea pedis or other fungal infections of the skin, the antifungal may be charged or uncharged. In some examples, the same or different antimicrobial or antifungal may be used topically following the treatment to provide for a continued effect once treatment is terminated.

In certain embodiments, devices other than footbaths may be used to treat the area having the loss of protective sensation. For example, where areas of the hands or legs are afflicted with loss of protective sensation, treatment may be difficult using a footbath. In such instances, a glove, sock, wrap, sleeve, bandage or similar devices can be used to treat loss of protective sensation in those areas. Illustrations of these devices are provided in more detail below. One or more circuits can be integrated into the devices to provide a desired current, voltage, pulse pair frequency or the like.

Figure 4A:
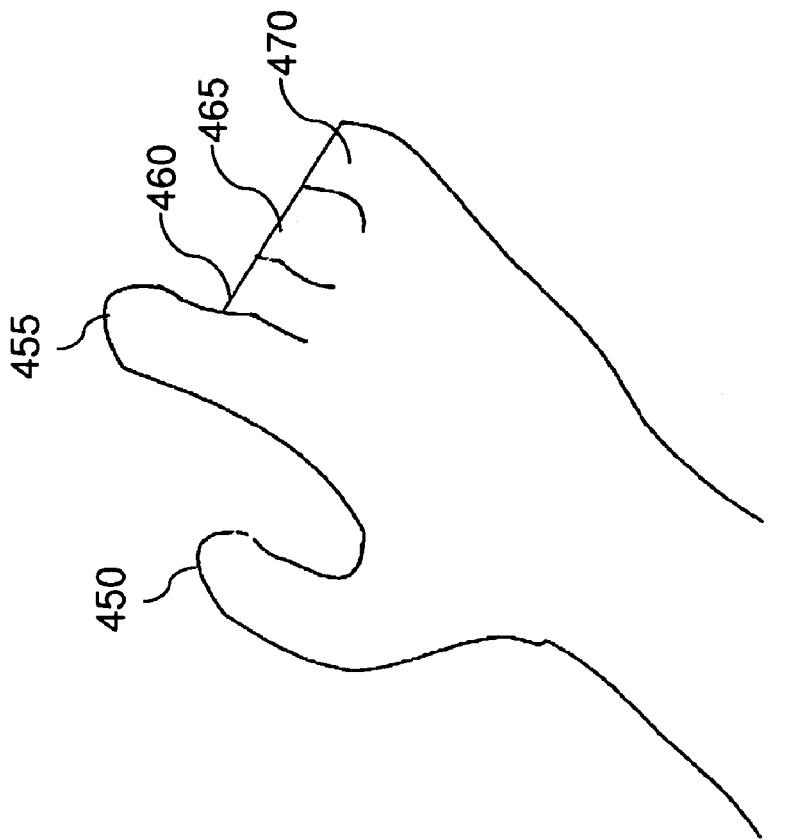
FIGS. 4A and 4B are illustrations of different glove embodiments, in accordance with certain examples.

In certain examples, a glove may be used to provide for treatment of the loss of protective sensation or other neuropathic conditions. One illustration of a glove is shown in FIG. 4A. The glove includes a plurality of finger receptacles 405, 410, 415, 420 and 425 attached to a palm surface 430 and a back surface (not shown), each extending from the finger receptacles toward a wrist portion 440. The glove may be sized and arranged to provide a tight fit over the subject's hand and may come in different sizes, e.g., small, medium and large, to facilitate such a tight fit. Two or more electrodes may be placed in the glove to facilitate treatment of the area having loss of protective sensation. The tight fit of the glove can act to maintain the position of the electrodes once inserted, or adhesives, tapes and the like may be used to hold the electrodes at a desired position. Alternatively, the glove may include a plurality of integral electrodes any two of which can be electrically coupled to a power source to provide treatment. The glove may include an on-board circuit that can provide a desired current form or intensity, e.g., the pulsed current forms and current parameters described herein, when the circuit is electrically coupled to a power source. In some examples, the glove may include an on-board power source, e.g., a watch battery or other disposable or rechargeable battery, that can be used to facilitate treatment while permitting movement of the subject. In some embodiments, a timing circuit may be integrated into the glove such that treatment is not performed too often by the subject, e.g., the timing circuit may permit a single treatment for thirty minutes within a 24 hour period.

Figure 4B:
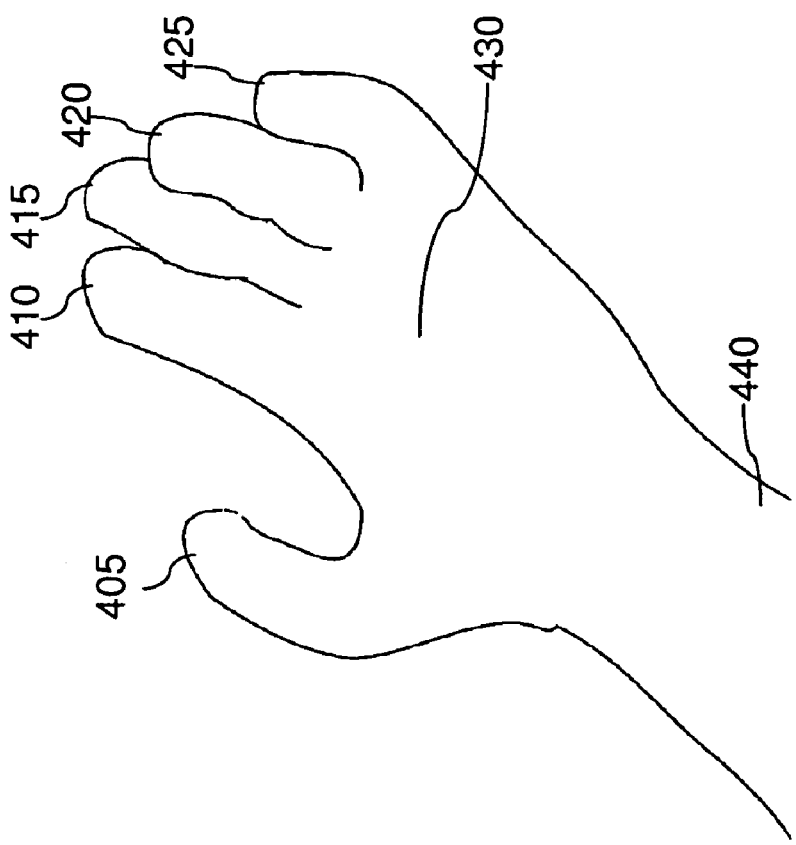

In certain embodiments, where the area of the hand having lost protective sensation (or other neuropathic conditions) is on a single finger, the glove may include fewer than five finger receptacles. One illustration of such a glove is shown in FIG. 4B. In this configuration, a thumb receptacle 450 and an index finger receptacle 455 are present, and openings 460, 465 and 470 are present in the other finger receptacles to permit the ends of the other fingers to exit the glove. In some embodiments, openings may be present in the glove such that the ends of all the fingers protrude. In some configurations, only one, two, three or four finger receptacles may be present. In addition, where two or more finger receptacles are present, the finger receptacles need not be adjacent to each other, e.g., a thumb receptacle and a ring finger receptacle may be the two finger receptacles present.

In certain examples, the glove, or portions thereof, may be made of a porous material to permit wetting of the area to be treated or wetting of the entire hand in the glove. Such wetting can facilitate delivery of the applied current to the affected area. Alternatively, a wet gauze pad or other material may be placed in the glove and on the area to be treated to facilitate treatment of loss of protective sensation or other neuropathic conditions in that area. If wetting of an area or areas is performed, then the fluid or fluids used to wet the area may be water, saline or other fluids described herein, e.g., those include a depolarizing agent. In some examples, the gloved area can be immersed and held in a fluid in the footbath prior to the treatment to maintain wetting of the area to be treated.

In certain embodiments, where a subject has loss of protective sensation or other neuropathic conditions on the feet and hands, treatment of both areas can be simultaneously performed using a footbath and using a glove. Such simultaneous treatment permits a reduction of overall treatment time while treating different areas experiencing loss of protective sensation (or other neuropathic conditions). In some examples, the glove and the footbath can be electrically coupled to the same power source or may be electrically coupled to different power sources. In addition, a calibration protocol as shown in FIG. 2, for example, may be performed separately for the areas on the hand and the areas on the foot to identify the current intensity that can be provided to each area without causing undue pain to the subject.

Figure 5:
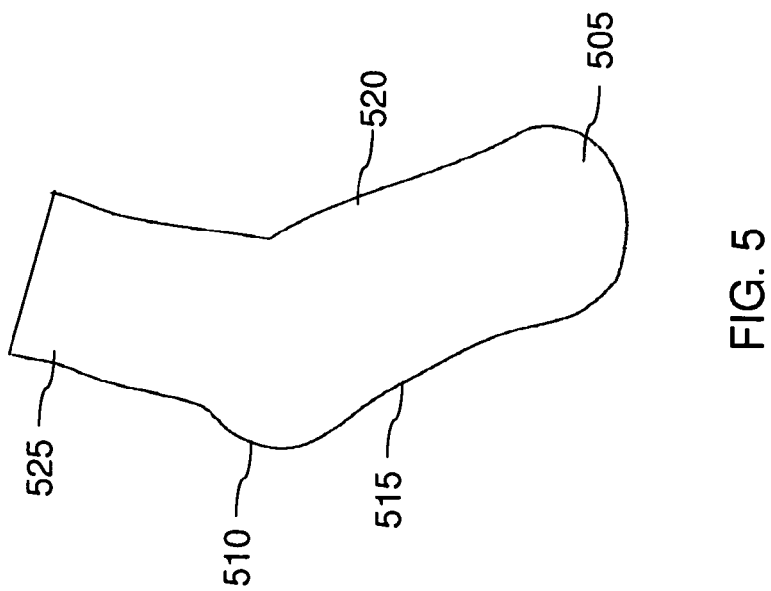
FIG. 5 is an illustration of a sock, in accordance with certain examples.

In certain embodiments, a sock for treating an area having loss of protective sensation or affected by another neuropathic condition is provided. One illustration of such a sock is shown in FIG. 5. The sock includes a toe segment 505, a heel segment 510, and a plantar segment 515 and a dorsal segment 520 each extending between the toe segment 505 and the heel segment 510 and connected to each other. The sock also includes an ankle segment 525 connected to the heel segment 510, the plantar segment 515 and the dorsal segment 520. Similar to the gloves described herein, the sock may be sized in multiple sizes, e.g., small, medium and large, such that the appropriate size can be selected to provide a suitable fit on the subject's foot.

In certain examples, the sock may include integrated electrodes such that two or more of the electrodes can be electrically coupled to a power source to provide current for the treatment. In some examples, the power source may be on board and take the form of a battery or other device that can provide limited power, whereas in other examples the power source may be external and coupled to the electrodes through one or more suitable electrical leads. In some examples, electrodes can be placed between the sock and the area of the foot to be treated and held in place generally through a friction fit. For example, an area or areas of the foot can be identified that have loss of protective sensation. Electrodes can be placed on or adjacent to the identified area to couple the electrodes to the area, and treatment may be performed by application of a suitable current. In an alternative embodiment, the sock may include an electrode at the toe segment 505 and another electrode at the heel segment 510. Each of these electrodes can be electrically coupled to a power source and treatment of the area may be effectuated by application of a current through the toe/heel electrode pair. Other suitable electrode positions for treating an area having loss of protective sensation will be selected by the person of ordinary skill in the art, given the benefit of this disclosure. Similar to the glove, a circuit can be integrated into sock to provide a desired current, voltage, pulse pair frequency or the like, or the power source can be configured to provide such desired features.

Figure 6A:
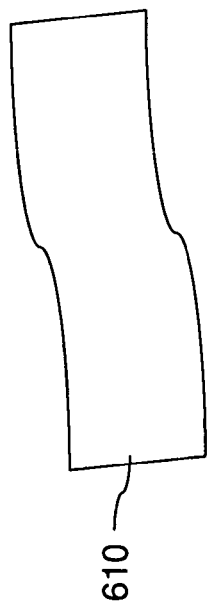
FIG. 6A is an illustration of a bandage.

In certain embodiments, the area or areas to be treated may be on a portion of a subject's body such that the footbath, sock or glove are not easily used or placed. In such instances, a bandage, wrap or sleeve may be placed on these areas. The bandage, sleeve or wrap may take many different forms depending on the area to be treated. Where a bandage is used, the bandage may include a generally planar or flat surface that can be placed over the area to be treated, as shown generally in the bandage 610 of FIG. 6A. The bandage may include integrated electrodes that can be coupled to a current source. Alternatively, electrodes may be placed on or near the area to be treated and the bandage can be placed over the electrodes to hold them in place. The bandage may include an adhesive or other material to stick to the area, or surrounding body portions, to be treated. In some embodiments, the bandage may be wet or wetted to facilitate delivery of the current to the area to treat the loss of protective sensation. In certain embodiments, the bandage can include a circuit configured to provide a desired current, voltage, pulse pair frequency or the like, or the power source can be configured to provide such desired features.

Figure 6B:
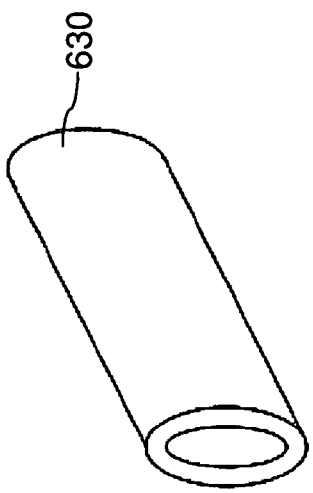
FIG. 6B is an illustration of a sleeve.

In certain embodiments, a sleeve may be placed around the area to be treated. The sleeve comprises a generally circular or cylindrical shape with an internal portion that permits part of an appendage to pass through, as shown in the sleeve 630 of FIG. 6B. Electrodes can be integrated into the sleeve or external electrodes can be used with the sleeve. The exact length and diameter of the sleeve can vary. In certain examples, the length of the sleeve is selected to cover the area or areas to be treated. In other examples, the diameter of the sleeve is selected to fit tightly around the area. Such tight fitting may hold the electrodes in place or where electrodes are integrated into the sleeve, the electrodes will be held in contact with or near the area to be treated. A current source can be connected to the electrodes to provide treatment to the area within the sleeve. Similar to the bandage, the sleeve may be wetted or areas under the sleeve may be wet to facilitate delivery of current to the area. In certain embodiments, the wrap can include a circuit configured to provide a desired current, voltage, pulse pair frequency or the like, or the power source can be configured to provide such desired features.

Figure 6C:
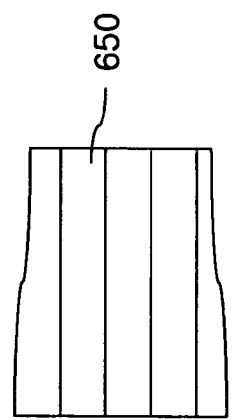
FIG. 6C is an illustration of a wrap, in accordance with certain examples.

In certain embodiments, the bandage or sleeve may not be suitable for placement near the area to be treated. In such instances, a wrap, such as wrap 650 shown in FIG. 6C, can be placed around the area and held in place using suitable fasteners such as for example, hook and loop fasteners, clips, tape or other materials or devices. In using the wrap, the wrap can be placed around the area to be treated and typically folds onto itself and is held in place using the fasteners, clips, tape or the like. Electrodes can be placed between the wrap and the area to be treated or the wrap may include electrodes itself. In some examples, the surfaces of the wrap that contact or are near the area to be treated include a plurality of electrodes that run from one side of the wrap to the other. Such a plurality of electrodes can facilitate treatment of the area without having to consider the effects of electrode placement on the treatment outcome. Where a plurality of electrodes are present, they may be arranged parallel to each other, in a grid pattern or in other selected patterns depending on the desired current profile to be provided to the area. Similar to the bandage and the sleeve, the area under the wrap can be wetted to enhance current delivery. Alternative, the entire wrap can be wet to enhance current delivery.

In certain embodiments, the exact type of current applied where a glove, sock, bandage, wrap or sleeve is used may be the same type of current applied using the footbath. For example, in certain embodiments the applied current may take the form of a direct current that is applied at less than 50 milliamperes, e.g., in either a continuous or pulsed form. In certain examples, the direct current can be applied using a voltage source less than 150 volts. In some examples, the direct current may be cycled between a fully on state, e.g., up to about 150 volts, and a fully off state, e.g., down to about 0 volts. The duration at which the current remains in the on state and the off state can vary and by cycling between the two states a current pulse can be generated. In certain embodiments, the effective amount of current can be provided using a monophasic pulsed current as described herein. In certain examples, the pulsed current can be provided at an intensity between about 500 microamperes to about 50 milliamperes, depending on the intensity that the subject can tolerate, in pulse pairs 150-330 microseconds apart, with a pulse width between 5-50 microseconds and a pulse pair repeat frequency of 100-200 Hz. The other illustrative current parameters described herein may also be implemented where a bandage, sock, wrap, glove or sleeve is used. A calibration step may also be performed where a glove, sock, bandage, wrap or sleeve is used. The calibration step may be performed to determine the maximum amount of tolerable current for use in the treatment. In addition, the bandage, wrap or sleeve may be used in combination with a footbath, glove or sock to treat many different areas simultaneously.

Figure 7:
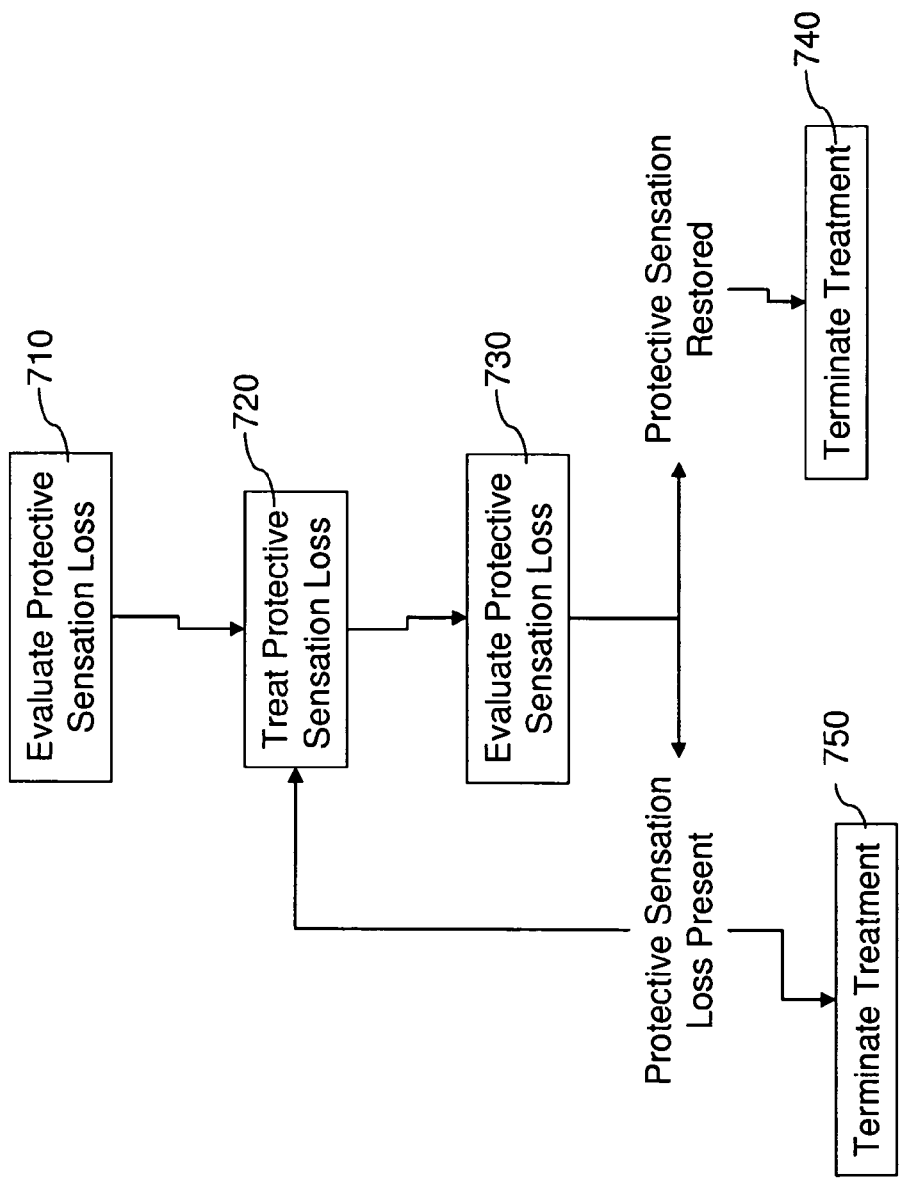
FIG. 7 is a protocol that can be used to assess treatment efficacy and termination, in accordance with certain examples.

In certain embodiments, depending on the severity of the loss of protective sensation (or other neuropathic condition), some subjects may need more treatment whereas other subjects may need less treatment to restore the protective sensation. To assess when treatment may be terminated, or the frequency of treatment may be reduced, the subject's protective sensation may be periodically reevaluated. An illustrative protocol is illustrated in FIG. 7. In a first step, the subject's protective sensation can be evaluated before a treatment at step 710. If there is protective sensation loss in one or more areas, the subject can be treated, as described herein, at step 720. The protective sensation loss can be reevaluated after the treatment at step 730, e.g., immediately after treatment or after some delay post-treatment. If protective sensation loss is still present, then another treatment can be performed. If protective sensation is partially restored, then another treatment can be performed. If protective sensation is restored, then treatment can be terminated at step 740. If after a selected treatment period, protective sensation loss is still present, then treatment may be terminated at step 750 based on the inability of successive treatments to restore protective sensation to the subject.

In certain examples, treatment may be continued until loss of protective sensation is restored. Restoration of protective sensation does not require that sensation return to an original state or return to normal nerve functioning. Instead, protective sensation is considered to be restored when a subject has enough sensation to detect ulcerations or passes a monofilament test or other suitable test. For example, treatment may be continued until there is at least a 100% improvement in protective sensation as measured using a monofilament test or other suitable test as compared to the pre-treatment protective sensation. In some examples, partial restoration of the protective sensation can be sufficient to provide a subject with the ability to sense pressure, to reduce or eliminate the risk of incurring damage such as ulcers or other disorders of the affected area. In certain embodiments, treatment may be continued until protective sensation improves by at least 10%, 20%, 30%, 40%, 50%, 60%, 70%, 80%, 90%, 100% or more.

In certain embodiments, treatment may be performed periodically once protective sensation is restored (or the symptoms or indicia of the neuropathic condition are reduced) to ensure protective sensation remains. For example, a subject whose protective sensation has been restored through treatment as described herein may once again lose protective sensation after treatment is terminated. In such instances, it may be desirable to periodically monitor the protective sensation of the subject, e.g., weekly, monthly, bimonthly, annually, etc., to ensure that the protective sensation remains. If loss of protective sensation reoccurs, then additional treatment can be initiated. Such maintenance treatment may occur at a lower frequency than the initial treatment used to restore the loss of protective sensation. In some examples, the embodiments described herein that facilitate subject movement during treatment, e.g., a sock, glove, sleeve, bandage, wrap or the like, may be intermittently used by the subject, e.g., once monthly, twice monthly, etc., as a prophylactic measure to ensure that the restored protective sensation is not lost again. Alternatively, treatment using a footbath or other suitable device can be used as a maintenance treatment.

In certain embodiments, the methods and devices disclosed herein can be used as a preventative measure for subjects at risk of loss of protective sensation. Such subjects typically include, but are not limited to, those subjects having prediabetes, diabetes, vascular disorders, exposure to toxins, or nutritional or metabolic disorders. When used as a preventative treatment, the treatment can be performed at a reduced frequency, e.g., weekly, biweekly, monthly, bi-monthly, semi-monthly, once every few months, once every six months, annually or the like. For example, subjects who are at risk for developing loss of protective sensation (or other neuropathic conditions) can be treated once annually during a routine physical examination. In addition, the current or voltage parameters used in preventative treatment can differ from those used to restore loss of protective sensation. In particular, the current intensity used can be less for preventative treatment than the current intensity used for restoration treatment.

In certain embodiments, the treatment methods and devices described herein can be co-administered with one or more drugs or therapeutics. For example, the treatment may be performed in combination with prescribing the subject an antidepressant, an anticonvulsant (such as, for example, a calcium channel blocker, a sodium channel blocker, pregabalin, gabapentin, carbamazepine and oxcarbazepine and the like), an opioid or opioid derivative (such as, for example, morphine, codeine, thebaine, hydrocodone, oxycodone, methadone, fentanyl, ketobimedone and the like), a topical agent (such as, for example, topical antifungals, antimicrobials, lacquers, vitamins, lidocaine, capsaicin and the like), a cannabinoid (Nabilone, a tetrahydrocannabinol), NMDA antagonists (such as, for example, ketamine and dextromethorphan), neuromodulating and neurostimulating substances and devices, therapeutics commonly used to treat diabetes (such as, for example, glyburide, metformin, insulin, or combinations thereof), oral or intravenous antibiotics, oral or intravenous antifungals, oral or intravenous antivirals, infusion pumps, anti-inflammatory drugs (such as, for example, ibuprofen, naproxen, aspirin, acetominophen, celecoxib or other selective COX-2 inhibitors) and combinations of these illustrative therapeutics and devices. Additional therapeutics and devices that can be co-administered with the treatment devices and methods described herein will be readily selected by the person of ordinary skill in the art, given the benefit of this specification. In some examples, post-treatment administration of a therapeutic may improve the overall treatment outcome. For example, where the subject has loss of protective sensation and one or more ulcers on the foot, oral, topical or intravenous administration of an antibiotic can act to prevent or treat any infection of the ulcers that could eventually lead to amputation.

In certain embodiments, the provided current may be advantageously utilized to simultaneously treat the loss of protective sensation and to drive a therapeutic into the area that is treated. For example, a charged drug may be provided in the fluid that is used for treatment (or used to wet an area), and application of the current to treat the loss of protective sensation can drive the charged drug into the area through iontophoresis. This process has the added benefit of increasing local drug concentrations in the area while providing the current to treat the loss of protective sensation.

In certain embodiments, the treatment devices and methods described herein can be used to simultaneously treat loss of protective sensation and one or more other disorders affecting the same area. For example, many diabetic patients have both loss of protective sensation and a fungal infection of the skin or nails of the feet (e.g., tinea pedis, onychomycosis, etc). The methods and devices described herein can be used to treat both disorders. The current parameters provided to treat the loss of protective sensation and the other disorder need not be the same. For example, a pulsed current can be provided to treat the loss of protective sensation while a direct current may be provided to treat onychomycosis (or vice versa). In certain embodiments, current parameters can be selected to simultaneously treat both loss of protective sensation and onychomycosis without having to provide differing current intensities, waveforms or other differing current parameters to treat both disorders. For example, current parameters can be selected to treat both loss of protective sensation and onychomycosis. Onychomycosis is a fungal infection of the nail and nail bed tissue that thickens, discolors, disfigures and/or destroys the nail. Nails can become thick and cause pressure, irritation and pain. Specific examples of subjects whose loss of protective sensation and onychomycosis were treated are described in more detail below.

In certain embodiments, a method of facilitating treatment of loss of protective sensation, or other neuropathic condition or disease, is provided. In some examples, the method comprises providing a footbath sized and arranged to receive one or both feet of the subject, the footbath comprising a reservoir comprising a front wall, sidewalls coupled to the front wall, a back wall coupled to the sidewalls and a bottom surface coupled to the front wall, the sidewalls and the back wall to provide a substantially fluid tight reservoir. In some examples, the method may also include providing a first electrode and a second electrode. In other examples, the method may include providing instructions to use the footbath to provide a pulsed current through the first and second electrodes to an area of the foot to treat the loss of protective sensation.

In certain examples, the instructions can include providing a monophasic pulsed current between about 500 microamperes and about 50 milliamperes, in pulse pairs about 150-330 microseconds apart, with a pulse width between about 5-50 microseconds and a pulse pair repeat frequency of about 100-200 Hz. In some embodiments, the instructions can include a calibrating step to determine the maximum current that can be tolerated by the subject for the treatment as described herein. In certain embodiments, the instructions can include a step to identify the area having the loss of protective sensation. In some examples, the instructions can include a treatment regimen specifying the frequency of treatment. In other examples, the method can comprise providing a power source configured to provide the pulsed current to the area through the first and second electrodes. In certain examples, the method can comprise providing a depolarizing agent. In additional examples, the method can include providing a monofilament to use in identifying the area having the loss of protective sensation. In certain embodiments, the method can include providing a therapeutic for co-administration with the treatment for the loss of protective sensation. In additional examples, the method can include instructions for evaluating the loss of protective sensation after the treatment.

In other embodiments, a method of facilitating treatment of loss of protective sensation (or other neuropathic condition) comprising providing a sock comprising a toe segment, a heel segment, a plantar segment extending between the toe segment and the heel segment, a dorsal segment extending between the heel segment and the toe segment and connected to the plantar segment is described. In some examples, the method can include providing a first electrode and a second electrode. In additional examples, the method can include providing instructions to use the sock to provide a pulsed current through the first and second electrodes to the area of a foot to treat the loss of protective sensation.

In certain embodiments, the instructions can include providing a monophasic pulsed current between about 500 microamperes and about 50 milliamperes, in pulse pairs about 150-330 microseconds apart, with a pulse width between about 5-50 microseconds and a pulse pair repeat frequency of about 100-200 Hz. In certain examples, the instructions can include a calibrating step to determine the maximum current that can be tolerated by the subject for the treatment. In some examples, the instructions can include a step to identify the area having the loss of protective sensation. In certain embodiments, the instructions can include a treatment regimen specifying the frequency of treatment. In some embodiments, the method can include providing a power source configured to provide the pulsed current through the first and second electrodes. In certain examples, the method can include providing a depolarizing agent. In other examples, the method can include providing a monofilament to use in identifying the area having the loss of protective sensation. In additional examples, the method can include providing a therapeutic for co-administration with the treatment for the loss of protective sensation.

In another embodiment, a method of facilitating treatment of loss of protective sensation (or other neuropathic condition) comprising providing a glove comprising at least one finger receptacle, a palm surface and a back surface each extending from the finger receptacle to a wrist portion is disclosed. In certain examples, the method can include providing a first electrode and a second electrode. In some examples, the method can include providing instructions to use the glove to provide a pulsed current through the first and second electrodes to the area of the hand to treat the loss of protective sensation.

In certain embodiments, the instructions can include providing a monophasic pulsed current between about 500 microamperes and about 50 milliamperes, in pulse pairs about 150-330 microseconds apart, with a pulse width between about 5-50 microseconds and a pulse pair repeat frequency of about 100-200 Hz. In some examples, the instructions can include a calibrating step to determine the maximum current that can be tolerated by the subject for the treatment. In certain examples, the instructions can include a step to identify the area having the loss of protective sensation. In some embodiments, the instructions can include a treatment regimen specifying the frequency of treatment. In other examples, the method can include providing a power source configured to provide the pulsed current through the first and second electrodes. In some examples, the method can include providing a depolarizing agent. In certain examples, the method can include providing a monofilament to use in identifying the area having the loss of protective sensation. In some embodiments, the method can include providing a therapeutic for co-administration with the treatment for the loss of protective sensation.

In an additional embodiment, a method of facilitating treatment of loss of protective sensation (or other neuropathic condition) comprising providing a sleeve configured to encompass an appendage comprising an area with loss of protective sensation is described. In certain embodiments, the method can include providing a first electrode and a second electrode. In other embodiments, the method can include providing instructions to use sleeve to provide a pulsed current through the first and second electrodes to the area to treat the loss of protective sensation.

In certain examples, the instructions can include providing a monophasic pulsed current between about 500 microamperes and about 50 milliamperes, in pulse pairs about 150-330 microseconds apart, with a pulse width between about 5-50 microseconds and a pulse pair repeat frequency of about 100-200 Hz. In other examples, the instructions can include a calibrating step to determine the maximum current that can be tolerated by the subject for the treatment. In additional examples, the instructions can include a step to identify the area having the loss of protective sensation. In some examples, the instructions can include a treatment regimen specifying the frequency of treatment. In other examples, the method can include providing a power source configured to provide the pulsed current through the first and second electrodes. In additional examples, the method can include providing a depolarizing agent. In other examples, the method can include providing a monofilament to use in identifying the area having the loss of protective sensation. In some examples, the method can include providing a therapeutic for co-administration with the treatment for the loss of protective sensation.

In another embodiment, a method of facilitating treatment of loss of protective sensation (or other neuropathic condition) comprising providing a bandage configured to be placed on an area with loss of protective sensation is disclosed. In certain examples, the method can include providing a first electrode and a second electrode. In other examples, the method can include providing instructions to use the bandage to provide a pulsed current through the first and second electrodes to the area to treat the loss of protective sensation.

In certain examples, the instructions can include providing a monophasic pulsed current between about 500 microamperes and about 50 milliamperes, in pulse pairs about 150-330 microseconds apart, with a pulse width between about 5-50 microseconds and a pulse pair repeat frequency of about 100-200 Hz. In other examples, the instructions can include a calibrating step to determine the maximum current that can be tolerated by the subject for the treatment. In additional examples, the instructions can include a step to identify the area having the loss of protective sensation. In some examples, the instructions can include a treatment regimen specifying the frequency of treatment. In certain embodiments, the method can include providing a power source configured to provide the pulsed current through the first and second electrodes. In some examples, the method can include providing a depolarizing agent. In certain examples, the method can include providing a monofilament to use in identifying the area having the loss of protective sensation. In additional examples, the method can include providing a therapeutic for co-administration with the treatment for the loss of protective sensation.

In an additional embodiment, a method of facilitating treatment of loss of protective sensation (or other neuropathic condition) comprising providing a wrap configured to be positioned around an area to be treated for the loss of protective sensation and configured to contact itself to retain the wrap around the area to be treated for the loss of protective sensation is described. In certain examples, the method can include providing a first electrode and a second electrode. In some examples, the method can include providing instructions to use the bandage to provide a pulsed current through the first and second electrode to the area to treat the loss of protective sensation.

In certain embodiments, the instructions can include providing a monophasic pulsed current between about 500 microamperes and about 50 milliamperes, in pulse pairs about 150-330 microseconds apart, with a pulse width between about 5-50 microseconds and a pulse pair repeat frequency of about 100-200 Hz. In some embodiments, the instructions can include a calibrating step to determine the maximum current that can be tolerated by the subject for the treatment. In other embodiments, the instructions can include a step to identify the area having the loss of protective sensation. In certain examples, the instructions can include a treatment regimen specifying the frequency of treatment. In some embodiments, the method can include providing a power source configured to provide the pulsed current through the first and second electrodes. In certain embodiments, the method can include providing a depolarizing agent. In some examples, the method can include providing a monofilament to use in identifying the area having the loss of protective sensation. In other examples, the method can include providing a therapeutic for co-administration with the treatment for the loss of protective sensation.

In another embodiments, a kit for treating loss of protective sensation (or other neuropathic condition) in an area of a foot comprising a footbath sized and arranged to receive one or both feet of the subject, the footbath having a reservoir comprising a front wall, sidewalls coupled to the front wall, a back wall coupled to the sidewalls and a bottom surface coupled to the front wall, the sidewalls and the back wall to provide a substantially fluid tight reservoir, and instructions to use the footbath to provide a pulsed current through a first electrode and a second electrode in the footbath to the area of the foot to treat the loss of protective sensation is described.

In certain embodiments, the kit with the footbath can include a power source. The power source, for example, can be configured to provide a monophasic pulsed current between about 500 microamperes and about 50 milliamperes, in pulse pairs about 150-330 microseconds apart, with a pulse width between about 5-50 microseconds and a pulse pair repeat frequency of about 100-200 Hz. In some examples, the kit can include a depolarizing agent. In other examples, the instructions can include a calibrating step to determine the maximum current that can be tolerated by the subject for the treatment. In some examples, the instructions can include a step to identify the area having the loss of protective sensation. In additional examples, the instructions can include a treatment regimen specifying the frequency of treatment. In some examples, the kit can include a depolarizing agent. In certain examples, the kit can include a monofilament to use in identifying the area with the loss of protective sensation. In other examples, the kit can include a therapeutic for co-administration with the treatment for the loss of protective sensation.

In another embodiment, a kit for treating loss of protective sensation (or other neuropathic condition) in an area of the foot comprising a sock comprising a toe segment, a heel segment, a plantar segment extending between the toe segment and the heel segment, a dorsal segment extending between the heel segment and the toe segment and connected to the plantar segment, and providing instructions to use the sock to provide a pulsed current through a first electrode and a second electrode in or on the sock to the area of a foot to treat the loss of protective sensation is disclosed.

In certain embodiments, the kit with the sock can include a power source. The power source, for example can be configured to provide a monophasic pulsed current between about 500 microamperes and about 50 milliamperes, in pulse pairs about 150-330 microseconds apart, with a pulse width between about 5-50 microseconds and a pulse pair repeat frequency of about 100-200 Hz. In some examples, the kit can include a depolarizing agent. In other examples, the instructions can include a calibrating step to determine the maximum current that can be tolerated by the subject for the treatment. In some examples, the instructions can include a step to identify the area having the loss of protective sensation. In additional examples, the instructions can include a treatment regimen specifying the frequency of treatment. In some examples, the kit can include a depolarizing agent. In certain examples, the kit can include a monofilament to use in identifying the area with the loss of protective sensation. In other examples, the kit can include a therapeutic for co-administration with the treatment for the loss of protective sensation.

In an additional embodiment, a kit for treating loss of protective sensation (or other neuropathic condition) on an area of a hand comprising a glove comprising at least one finger receptacle, a palm surface and a back surface each extending from the finger receptacle to a wrist portion, and instructions to use the glove to provide a pulsed current to a first electrode and a second electrode in or in contact with the glove to the area of the hand to treat the loss of protective sensation is disclosed.

In certain embodiments, the kit with the glove can include a power source. The power source, for example, can be configured to provide a monophasic pulsed current between about 500 microamperes and about 50 milliamperes, in pulse pairs about 150-330 microseconds apart, with a pulse width between about 5-50 microseconds and a pulse pair repeat frequency of about 100-200 Hz. In some examples, the kit can include a depolarizing agent. In other examples, the instructions can include a calibrating step to determine the maximum current that can be tolerated by the subject for the treatment. In some examples, the instructions can include a step to identify the area having the loss of protective sensation. In additional examples, the instructions can include a treatment regimen specifying the frequency of treatment. In some examples, the kit can include a depolarizing agent. In certain examples, the kit can include a monofilament to use in identifying the area with the loss of protective sensation. In other examples, the kit can include a therapeutic for co-administration with the treatment for the loss of protective sensation.

In an additional embodiment, a kit for treating loss of protective sensation (or other neuropathic condition) comprising a sleeve configured to encompass an appendage comprising an area with loss of protective sensation, and instructions to use the sleeve to provide a pulsed current through a first electrode and a second electrode in or on the sleeve to the area to treat the loss of protective sensation is disclosed.

In certain embodiments, the kit with the sleeve can include a power source. The power source, for example, can be configured to provide a monophasic pulsed current between about 500 microamperes and about 50 milliamperes, in pulse pairs about 150-330 microseconds apart, with a pulse width between about 5-50 microseconds and a pulse pair repeat frequency of about 100-200 Hz. In some examples, the kit can include a depolarizing agent. In other examples, the instructions can include a calibrating step to determine the maximum current that can be tolerated by the subject for the treatment. In some examples, the instructions can include a step to identify the area having the loss of protective sensation. In additional examples, the instructions can include a treatment regimen specifying the frequency of treatment. In some examples, the kit can include a depolarizing agent. In certain examples, the kit can include a monofilament to use in identifying the area with the loss of protective sensation. In other examples, the kit can include a therapeutic for co-administration with the treatment for the loss of protective sensation.

In another embodiment, a kit for treating loss of protective sensation (or other neuropathic condition) comprising a bandage configured to be placed on an area with loss of protective sensation, and instructions to use the bandage to provide a pulsed current through a first electrode and a second electrode in or in on the bandage to the area to treat the loss of protective sensation is described.

In certain embodiments, the kit with the bandage can include a power source. The power source, for example can be configured to provide a monophasic pulsed current between about 500 microamperes and about 50 milliamperes, in pulse pairs about 150-330 microseconds apart, with a pulse width between about 5-50 microseconds and a pulse pair repeat frequency of about 100-200 Hz. In some examples, the kit can include a depolarizing agent. In other examples, the instructions can include a calibrating step to determine the maximum current that can be tolerated by the subject for the treatment. In some examples, the instructions can include a step to identify the area having the loss of protective sensation. In additional examples, the instructions can include a treatment regimen specifying the frequency of treatment. In some examples, the kit can include a depolarizing agent. In certain examples, the kit can include a monofilament to use in identifying the area with the loss of protective sensation. In other examples, the kit can include a therapeutic for co-administration with the treatment for the loss of protective sensation.

In another embodiment, a kit for facilitating treatment of loss of protective sensation (or other neuropathic condition) comprising a wrap configured to be positioned around an area to be treated for the loss of protective sensation and configured to contact itself to retain the wrap around the area to be treated for the loss of protective sensation, and instructions to use the wrap to provide a pulsed current through a first electrode and a second electrode in or in on the wrap to the area to treat the loss of protective sensation is described.

In certain embodiments, the kit with the wrap can include a power source. The power source, for example can be configured to provide a monophasic pulsed current between about 500 microamperes and about 50 milliamperes, in pulse pairs about 150-330 microseconds apart, with a pulse width between about 5-50 microseconds and a pulse pair repeat frequency of about 100-200 Hz. In some examples, the kit can include a depolarizing agent. In other examples, the instructions can include a calibrating step to determine the maximum current that can be tolerated by the subject for the treatment. In some examples, the instructions can include a step to identify the area having the loss of protective sensation. In additional examples, the instructions can include a treatment regimen specifying the frequency of treatment. In some examples, the kit can include a depolarizing agent. In certain examples, the kit can include a monofilament to use in identifying the area with the loss of protective sensation. In other examples, the kit can include a therapeutic for co-administration with the treatment for the loss of protective sensation.

In certain embodiments, the methods described herein can be implemented using a computer or other device that includes a processor or the devices described herein can be electrically coupled to a computer system or processor. Such computer implemented methods can facilitate treatment and reduce operator error. In addition, the computer can track the number of treatments, recall current parameters and increase the overall ease of providing the treatment. The computer system typically includes at least one processor optionally electrically coupled with one or more memory units. The computer system may be, for example, a general-purpose computer such as those based on Unix, Intel PENTIUM-type processor, Motorola PowerPC, Sun UltraSPARC, Hewlett-Packard PA-RISC processors, or any other type of processor. In some examples, the processor may be an inexpensive processor that may be programmable to receive inputs and output treatment parameters based on the received inputs. It should be appreciated that one or more of any type computer system may be used according to various embodiments of the technology. Further, the system may be located on a single computer or may be distributed among a plurality of computers attached by a communications network. A general-purpose computer system may be configured, for example, to perform any of the described functions including but not limited to: current application, treatment frequency tracking, treatment time, subject tracking and the like. It should be appreciated that the system may perform other functions, including network communication, and the technology is not limited to having any particular function or set of functions.

For example, various aspects may be implemented as specialized software executing in a general-purpose computer system. The computer system may include a processor connected to one or more memory devices, such as a disk drive, memory, or other device for storing data. Memory is typically used for storing programs and data during operation of the computer system. Components of the computer system may be coupled by an interconnection device, which may include one or more buses (e.g., between components that are integrated within a same machine) and/or a network (e.g., between components that reside on separate discrete machines). The interconnection device provides for communications (e.g., signals, data, instructions) to be exchanged between components of the system. The computer system typically is electrically coupled to the power source and/or electrodes such that electrical signals may be provided to and from the power source and/or electrodes to provide the desired treatment or for storage and/or processing. The computer system may also include one or more input devices, for example, a keyboard, mouse, trackball, microphone, touch screen, manual switch (e.g., override switch) and one or more output devices, for example, a printing device, display screen, speaker. In addition, the computer system may contain one or more interfaces that connect the computer system to a communication network (in addition or as an alternative to the interconnection device).

The storage system typically includes a computer readable and writeable nonvolatile recording medium in which signals are stored that define a program to be executed by the processor or information stored on or in the medium to be processed by the program. For example, the treatment times, current parameters, areas having loss of protective sensation and the like for a particular subject may be stored on the medium. The medium may, for example, be a disk or flash memory. Typically, in operation, the processor causes data to be read from the nonvolatile recording medium into another memory that allows for faster access to the information by the processor than does the medium. This memory is typically a volatile, random access memory such as a dynamic random access memory (DRAM) or static memory (SRAM). It may be located in the storage system or in the memory system. The processor generally manipulates the data within the integrated circuit memory and then copies the data to the medium after processing is completed. A variety of mechanisms are known for managing data movement between the medium and the integrated circuit memory element and the technology is not limited thereto. The technology is also not limited to a particular memory system or storage system.

In certain examples, the computer system may also include specially-programmed, special-purpose hardware, for example, an application-specific integrated circuit (ASIC) or a field programmable gate array (FPGA). Aspects of the technology may be implemented in software, hardware or firmware, or any combination thereof. Further, such methods, acts, systems, system elements and components thereof may be implemented as part of the computer system described above or as an independent component.

Although a computer system is described by way of example as one type of computer system upon which various aspects of the technology may be practiced, it should be appreciated that aspects are not limited to being implemented on the described computer system. Various aspects may be practiced on one or more computers having a different architecture or components. The computer system may be a general-purpose computer system that is programmable using a high-level computer programming language. The computer system may be also implemented using specially programmed, special purpose hardware. In the computer system, the processor is typically a commercially available processor such as the well-known Pentium class processor available from the Intel Corporation. Many other processors are available. Such a processor usually executes an operating system which may be, for example, the Windows 95, Windows 98, Windows NT, Windows 2000 (Windows ME), Windows XP or Windows Vista operating systems available from the Microsoft Corporation, MAC OS System X operating system available from Apple Computer, the Solaris operating system available from Sun Microsystems, or UNIX or Linux operating systems available from various sources. Many other operating systems may be used, and in certain embodiments a simple set of commands or instructions may function as the operating system.

In accordance with certain examples, the processor and operating system may together define a computer platform for which application programs in high-level programming languages may be written. It should be understood that the technology is not limited to a particular computer system platform, processor, operating system, or network. Also, it should be apparent to those skilled in the art, given the benefit of this disclosure, that the present technology is not limited to a specific programming language or computer system. Further, it should be appreciated that other appropriate programming languages and other appropriate computer systems could also be used. In certain examples, the hardware or software is configured to implement cognitive architecture, neural networks or other suitable implementations.

One or more portions of the computer system may be distributed across one or more computer systems coupled to a communications network. These computer systems also may be general-purpose computer systems. For example, various aspects may be distributed among one or more computer systems configured to provide a service (e.g., servers) to one or more client computers, or to perform an overall task as part of a distributed system. For example, various aspects may be performed on a client-server or multi-tier system that includes components distributed among one or more server systems that perform various functions according to various embodiments. These components may be executable, intermediate (e.g., IL) or interpreted (e.g., Java) code which communicate over a communication network (e.g., the Internet) using a communication protocol (e.g., TCP/IP). It should also be appreciated that the technology is not limited to executing on any particular system or group of systems. Also, it should be appreciated that the technology is not limited to any particular distributed architecture, network, or communication protocol.

In accordance with certain examples, various embodiments may be programmed using an object-oriented programming language, such as SmallTalk, Basic, Java, C++, Ada, or C# (C-Sharp). Other object-oriented programming languages may also be used. Alternatively, functional, scripting, and/or logical programming languages may be used. Various configurations may be implemented in a non-programmed environment (e.g., documents created in HTML, XML or other format that, when viewed in a window of a browser program, render aspects of a graphical-user interface (GUI) or perform other functions). Certain configurations may be implemented as programmed or non-programmed elements, or any combination thereof.

In certain examples, a user interface may be provided such that a user may enter a subject's information, treatment parameters or other data desired. For example, in instances where a patient has already received treatment, relevant treatment parameters may be recalled and reused without the need to determine current parameters or the like by entering the subject's name or identified in the appropriate field of the graphical user interface. Other features for inclusion in a user interface will be readily selected by the person of ordinary skill in the art, given the benefit of this disclosure.

Certain specific examples are described below to illustrate further some of the aspects and features described herein.

EXAMPLE 1

Subjects were identified as having loss of protective sensation on a foot using the 10-g Semmes-Weinstein Monofilament test described herein. Subjects having identified areas with loss of protective sensation were instructed to sit in a flat high back chair and the feet were inspected for any foot irritation, skin breaks or bruising. One end of a pair of electrodes (Mettler Electronics PN:2002) were attached to a foot basin (Sterilite PN:0658). The other end of the pair of electrodes were attached to a Rich-Mar System (Theratouch Model 4.7). The subject's target foot was placed in the foot basin with at least one toe contacting, or in close proximity to, one electrode and the heel contacting the other electrode. Disposable gauze was positioned between the heel of the foot and the electrode. The basin was filled with tap water until the malleolus was submerged. Hydrogen peroxide (16 ounces of a 3% $H_2O_2$ solution) was added to the tap water. The power on the Rich-Mar system was switched on. Position #1 was selected by turning the dial to "Wave" and pressing the dial. The waveform was selected by turning the dial to "Monophasic" and pressing the dial. The treatment mode was selected by turning the dial to "Continuous" and pressing the dial. The treatment time was selected by turning the dial to "Set" and pressing the dial. The dial was then turned to 30 minutes and pressed again. The pulse rate was set by turning the dial to 120 and pressing the dial. The phase interval was set by turning the dial to 100 and pressing the dial.

The current intensity for treatment was determined by increasing the intensity from zero to a comfortable level of subject perception up to a maximum of 40 mA. If the subject was uncomfortable with 40 mA, the current intensity was decreased incrementally until a comfortable level was obtained. Treatment was performed for thirty minutes. After treatment, the foot was removed from the foot basin and dried with a clean, disposable paper towel. The skin was then inspected for bruising, skin breaks, irritation or other signs of concern. The above-treatment was performed one time per day, five times per week for six weeks. The results are summarized in Table I.

TABLE I

| Subject No. | Areas with Loss of Protective Sensation before Treatment | 15 days after beginning treatment | 30 after beginning treatment | 30 days following termination of treatment | 90 days following termination of treatment | Final % Improvement |
|---|---|---|---|---|---|---|
| 16 | 4 Sites | 1 Site | 0 Sites | 0 Sites | 0 Sites | 100% |
| 35 | 8 Sites | 6 Sites | 1 Site | 1 Sites | 0 Sites | 100% |
| 36 | 10 Sites | 8 Sites | 3 Sites | 0 Sites | 0 Sites | 100% |
| 50 | 4 Sites | 2 Sites | 0 Sites | 0 Sites | 0 Sites | 100% |
| 57 | 9 Sites | 0 Sites | 0 Sites | 0 Sites | 0 Sites | 100% |

All subjects experienced 100% improvement in protective sensation 90 days following termination of the treatment. The results shown in Table I are consistent with treatment of loss of protective sensation using a current.

EXAMPLE 2

Subjects were identified for the presence of onychomycosis on one or more nails. Some of these subjects were the same subjects used in Example 1 and the subject numbering in Example 1 tracks the subject numbering in this example.

The length of clear nail from the cuticle to the most proximal point of infection, percent involvement of the infection and toenail thickness were measured. The subject's toenails were trimmed, and a sample was used for culturing and KOH testing to confirm the presence of fungus. A positive culture was confirmed for the presence of *Trichophyton rubrum, T. mentagrophytes* and/or *Epidermophyton floccosum.*

The onychomycosis was treated using the same protocol described in Example 1. Nail growth, nail appearance and skin integrity were assessed at the end of the six week treatment period. The results are summarized in Table II below. In Table II, the nail growth column refers to +1, +2, +3 or N/A. These values refer to a 25% increase in the nail length (+1), a 50% increase in the nail length (+2) or a 75% increase in the nail length (+3) as compared to the nail length prior to treatment. N/A refers to not performed.

TABLE II

| Subject No. | Sex | Age | Nail Growth | Skin Integrity | Nail Appearance |
|---|---|---|---|---|---|
| 12 | F | 89 | +2 | Improved | Improved |
| 13 | M | 82 | +2 | Improved | Altered |
| 14 | F | 93 | +2 | Significant Change | Significant Change |
| 16 | M | 89 | +2 | Improved | Improved |
| 30 | M | 86 | +2 | Improved | Improved |
| 34 | M | 83 | +1 | Improved | Improved |
| 35 | M | 91 | +1 | Improved | No Change |
| 36 | M | 87 | +2 | Improved | Improved |
| 45 | F | 89 | +1 | No Change | Subtle Change |
| 48 | N/A | N/A | N/A | N/A | N/A |
| 49 | F | 84 | +2 | Improved | Improved |
| 50 | F | 93 | +2 | Improved | Changes Noted |
| 52 | F | 41 | N/A | Improved | Improved |
| 57 | F | 71 | +3 | Improved | Changes Noted |
| 62 | M | 46 | +1 | No Change | Subtle Change |

The results shown in Table II are consistent with application of a current to treat onychomycosis and with application of a current to treat both onychomycosis and loss of protective sensation simultaneously.

When introducing elements of the examples disclosed herein, the articles "a," "an," "the" and "said" are intended to mean that there are one or more of the elements. The terms "comprising," "including" and "having" are intended to be open-ended and mean that there may be additional elements other than the listed elements. It will be recognized by the person of ordinary skill in the art, given the benefit of this disclosure, that various components of the examples can be interchanged or substituted with various components in other examples.

Although certain aspects, examples and embodiments have been described above, it will be recognized by the person of ordinary skill in the art, given the benefit of this disclosure, that additions, substitutions, modifications, and alterations of the disclosed illustrative aspects, examples and embodiments are possible.

What is claimed is:

1. A method of treating loss of protective sensation comprising:
    identifying an area with loss of protective sensation on a foot of a subject;
    placing the area in a footbath comprising a first electrode and a second electrode to immerse the area in a fluid in the footbath and to couple the foot to the first electrode and the second electrode; and
    providing an effective amount of a current to the area using the first electrode and the second electrode to treat the loss of protective sensation in the area of the foot, wherein the effective amount of current is provided as a pulsed current at an effective frequency of at least 100 Hz to selectively target sensory nerve fibers without targeting pain fibers.

2. The method of claim 1, in which the identifying step comprises subjecting the foot of the subject to a monofilament test to identify the area having loss of protective sensation.

3. The method of claim 1, in which the placing step comprises positioning at least one toe of the foot to be adjacent to or to contact the first electrode and positioning the heel of the foot proximal to or in contact with the second electrode.

4. The method of claim 1, in which the providing the effective amount of current step comprises providing a monophasic pulsed current between about 50 microamperes and about 50 milliamperes, in pulse pairs about 150-330 microseconds apart, with a pulse width between about 5-50 microseconds and a pulse pair repeat frequency of about 100-200 Hz.

5. The method of claim 1, in which the providing the current step comprises using a voltage source less than 150 volts.

6. The method of claim 5, in which the voltage source of less than 150 volts provides a pulsed current wherein each pulse rises to an amplitude of about 150 volts and returns to an amplitude of about 0 volts.

7. The method of claim 5, further comprising increasing intensity of the provided current until the subject can sense the provided current.

8. The method of claim 1, further comprising providing the effective amount of the current in the presence of a depolarizing agent.

9. The method of claim 1, further comprising providing the effective amount of current for thirty minutes, five times per week for six weeks to treat the loss of protective sensation of the area.

10. The method of claim 2, in which treatment is discontinued once sensation is restored to the area as measured using the monofilament test.

11. A method of treating loss of protective sensation of an area of an appendage of a subject, the method comprising:
    coupling the area of the appendage to a first electrode and a second electrode;
    providing an effective amount of a current to the coupled area through the first and second electrodes with a pulsed current provided at an effective frequency of at least 100 Hz to selectively target sensory nerve fibers without targeting pain fibers in the area of the appendage to treat the loss of protective sensation.

12. The method of claim 11, in which the effective amount of the current to selectively target sensory nerve fibers in the area of the appendage is provided using a footbath comprising the first electrode and the second electrode.

13. The method of claim 11, in which the effective amount of the current to selectively target sensory nerve fibers in the area of the appendage is provided using a sock, patch or a glove that includes the first electrode and the second electrode.

14. The method of claim 13, in which the sock, patch or glove further comprises an on-board power source.

15. The method of claim 11, in which the pulsed current is provided using a monophasic pulsed current between 500 microamperes and 50 milliamperes, in pulse pairs about 150-330 microseconds apart, with a pulse width between about 5-50 microseconds and a pulse pair repeat frequency of about 100-200 Hz.

16. The method of claim 11, in which the pulsed current is provided using a voltage source less than 150 volts.

17. The method of claim 11, in which the voltage source of less than 150 volts provides the pulsed current wherein each pulse rises to an amplitude of about 150 volts and returns to an amplitude of about 0 volts.

18. The method of claim 11, further comprising wetting the area of the appendage with the loss of protective sensation prior to providing the pulsed current to the coupled area.

19. A method of treating loss of protective sensation in an area of an appendage of a subject, the method comprising providing an effective amount of a pulsed current to the area with the neuropathy, the pulsed current provided at an effective pulse pair frequency of at least 100 Hz to selectively target sensory nerve fibers without substantial targeting of pain nerve fibers to treat the neuropathy in the area.

20. The method of claim 19, in which the appendage is a foot and the area is on the bottom of the foot, and which the pulsed current is provided by immersing the bottom of the foot in a footbath comprising a first and a second electrode coupled to the area.

21. The method of claim 19, in which the appendage is a hand and the pulsed current is provided by wetting the area of the hand and coupling a first electrode and a second electrode to the hand.

22. The method of claim 19, in which the effective amount of current is configured as a monophasic pulsed current between about 500 microamperes to about 50 milliamperes, in pulse pairs about 150-330 microseconds apart, with a pulse width between about 5-50 microseconds and a pulse pair repeat frequency of about 100-200 Hz and a symptom of the neuropathy is loss of protective sensation.

23. The method of claim 19, in which the effective amount of current is provided using a voltage source less than 150 volts and wherein each pulse rises to an amplitude of about 150 volts and returns to an amplitude of about 0 volts.

* * * * *